United States Patent
Hill et al.

[11] Patent Number: 6,045,571
[45] Date of Patent: Apr. 4, 2000

[54] MULTIFILAMENT SURGICAL CORD

[75] Inventors: Donald G. Hill, Hopatcong; Margaret D'Aversa, Whitehouse Station; Ilya S. Koyfman, Ringoes; Ralph Louis Spengler, Long Valley; Crawford R. Britt, South Plainfield, all of N.J.; Robert J. Cerwin, Pipersville, Pa.; Hal Brent Woodrow, Princeton, N.J.

[73] Assignee: Ethicon, Inc., Somerville, N.J.

[21] Appl. No.: 09/323,656

[22] Filed: Jun. 1, 1999

Related U.S. Application Data

[60] Provisional application No. 60/129,184, Apr. 14, 1999.

[51] Int. Cl.⁷ .................................................. A61B 17/04
[52] U.S. Cl. ............................................ 606/228; 606/230
[58] Field of Search ........................... 87/8, 13; 606/231, 606/228, 230

[56] References Cited

U.S. PATENT DOCUMENTS

| | | | |
|---|---|---|---|
| 3,130,728 | 4/1964 | Pearson et al. | 128/335.5 |
| 3,297,033 | 1/1967 | Schmitt et al. | 128/335.5 |
| 3,531,561 | 9/1970 | Trehu | 264/210 |
| 3,565,077 | 2/1971 | Glick | 128/335.5 |
| 3,626,948 | 12/1971 | Glick et al. | 128/335.5 |
| 3,636,956 | 1/1972 | Schneider | 128/335.5 |
| 3,839,524 | 10/1974 | Adams et al. | 264/102 |
| 3,849,185 | 11/1974 | Shepherd et al. | 117/161 |
| 3,942,532 | 3/1976 | Hunter et al. | 128/335.5 |
| 3,949,755 | 4/1976 | Vauquois | 128/335.5 |
| 4,014,973 | 3/1977 | Thompson | 264/290 R |
| 4,024,871 | 5/1977 | Stephenson | 128/335.5 |
| 4,027,676 | 6/1977 | Mattei | 128/335.5 |
| 4,043,344 | 8/1977 | Landi et al. | 128/335.5 |
| 4,047,533 | 9/1977 | Perciaccante et al. | 128/335.5 |
| 4,052,988 | 10/1977 | Doddi et al. | 128/92 |
| 4,510,934 | 4/1985 | Batra | 128/335.5 |
| 4,662,886 | 5/1987 | Moorse et al. | 623/13 |
| 4,942,875 | 7/1990 | Hlavacek et al. | 606/230 |
| 4,946,467 | 8/1990 | Oho et al. | 606/228 |
| 4,959,069 | 9/1990 | Brennan et al. | 606/228 |
| 4,983,180 | 1/1991 | Kawai et al. | 606/230 |
| 5,019,093 | 5/1991 | Kaplan et al. | 606/230 |
| 5,037,429 | 8/1991 | Hermes et al. | 606/228 |
| 5,051,272 | 9/1991 | Hermes et al. | 427/2 |
| 5,059,213 | 10/1991 | Chesterfield et al. | 606/228 |
| 5,123,912 | 6/1992 | Kaplan et al. | 606/230 |
| 5,133,738 | 7/1992 | Korthoff et al. | 606/224 |
| 5,181,923 | 1/1993 | Chesterfield et al. | 606/228 |
| 5,261,886 | 11/1993 | Chesterfield et al. | 606/228 |
| 5,306,289 | 4/1994 | Kaplan et al. | 606/228 |
| 5,314,446 | 5/1994 | Hunter et al. | 606/231 |
| 5,456,697 | 10/1995 | Chesterfield et al. | 606/228 |
| 5,662,682 | 9/1997 | Chesterfield et al. | 606/228 |

FOREIGN PATENT DOCUMENTS

| | | | |
|---|---|---|---|
| 0241252 | 6/1987 | European Pat. Off. | A61L 27/00 |
| 29 49 920 A1 | 3/1981 | Germany | A61L 17/00 |
| 752443 | 7/1956 | United Kingdom . | |
| 1091669 | 11/1967 | United Kingdom | A61I 17/00 |
| 1 332 505 | 10/1973 | United Kingdom | D01F 7/04 |
| 2 008 135 | 5/1979 | United Kingdom | C08G 63/76 |
| 2 082 213 | 3/1982 | United Kingdom | D04C 1/12 |
| 2 159 846 | 12/1985 | United Kingdom | D02G 3/36 |
| WO 92 10137 | 6/1992 | WIPO | A61B 17/00 |

Primary Examiner—Michael Buiz
Assistant Examiner—Anthony S. King

[57] ABSTRACT

A surgical cord comprising a interlocking multifilament sheath and an interlocked multifilament core. The interlocking multifilament core construction is characterized by being braided or knitted; preferred are braided cores with a pick counts ranging between 5 and 40.

30 Claims, 5 Drawing Sheets

MULTIFILAMENT SURGICAL CORD

This application claims benefit of Provisional Application Ser. No. 60/129,184 filed Apr. 14, 1999.

BACKGROUND OF THE INVENTION

This invention relates to an improved surgical cord containing an interlocked multifilament core. The interlocking multifilament core construction is characterized by being braided or knitted; preferred are braided cores with a pick counts ranging between 5 and 40.

THE FIELD OF THE INVENTION

Surgical sutures intended for the repair of body tissues must meet certain requirements such as biocompatability, sterilizability, good tensile properties, diameter uniformity, and provide acceptable knot-tying and knot-holding characteristics. In addition, in the case of absorbable sutures, they must have a controlled loss of mass and strength.

Figure 1:
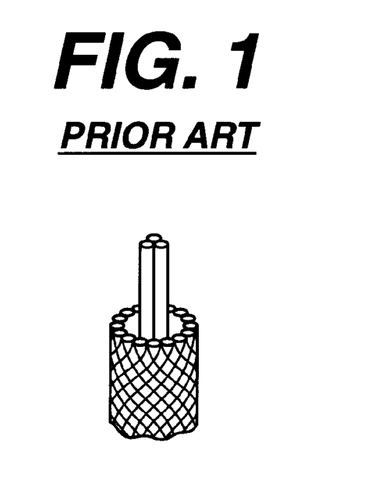
FIG. 1, is a perspective view of a prior art size 2/0 (USP) braided suture with a three ply non-twisted core and a sixteen (16) carrier braided sheath.
Figure 1A:
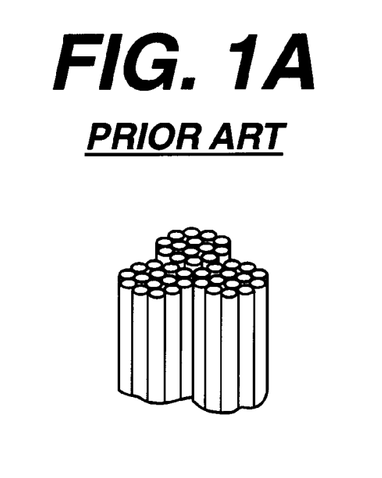
FIG. 1A an enlarged view of the three ply core of the suture.
Figure 1B:
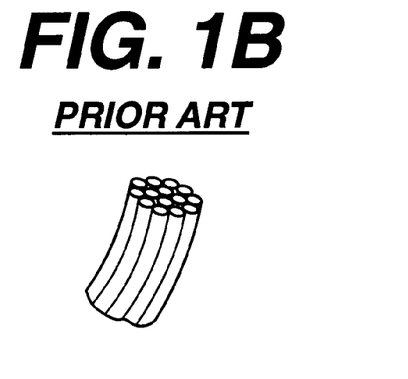
FIG. 1B is an enlarged view of the non-twisted yarn in the core.
Figure 2:
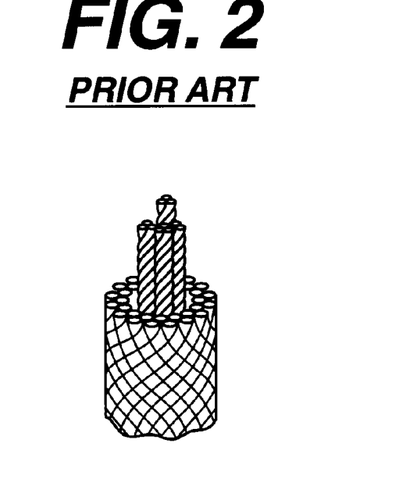
FIG. 2 is a perspective view of a prior art size 2 (USP) braided suture with a four strand three ply (with six (6) twists per inch) core and a sixteen carrier braided sheath.
Figure 2A:
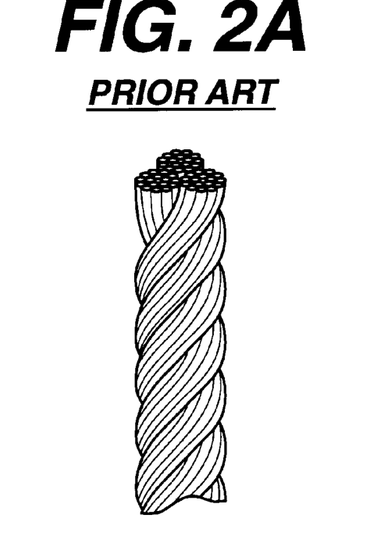
FIG. 2A an elarged view of one of the four three ply yarns of the core.
Figure 2B:
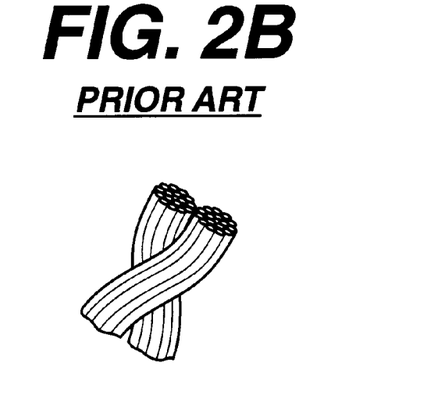
FIG. 2B an enlarged view of the twisted yarns in the core.

Surgical sutures can be made from a variety of materials such as surgical gut, cotton, silk, polypropylene, polyester, polyamide, polyglycolide, polylactide, and polylactide-glycolide copolymer, etc. Sutures can be manufactured in the form of monofilaments or multifilaments. Monofilament sutures are highly regarded for their uniform, smooth surface. Such a surface reduces tissue drag and possibly the chance of infection. However, monofilament sutures are generally fairly stiff, more difficult to tie and exhibit reduced knot security as compared to multifilament sutures. Multifilament sutures are usually constructed of tubular braid. FIGS. 1 and 2 illustrate conventional braided suture constructions. In larger suture sizes, in addition to the braided tubular sheath, a core is required to maintain a circular cross sectional shape and provide the required tensile strength.

Currently available braided sutures with central cores are acceptable in terms of their performance characteristics, but, quite often exhibit "core pops", the tendency of the core yarns to pop through the braid sheath when the suture is handled during manufacture or during knot tying. "Core pops" do not generally alter suture performance characteristics, such as tensile strength, knot tie-down and knot security properties; however, the visual appearance of a suture with core pops is not desirable to surgeons. Also, there is a belief that core pops may adversely effect tissue drag characteristics of the suture.

Although we do not wish to be held to scientific or engineering principle, we believe that the phenomenon of "core popping" may be attributed to sheath and core yarn relaxation from tension stresses acquired during braiding. When the braid is off-the-braider and in a relaxed condition (no tension applied), a reduction in length will occur (so-called braid shrinkage). The percentage of sheath shrinkage is higher than that of core resulting in extra core in the braid. This in turn leads to the presence of braid bumps. When a braid is manipulated during processing and/or knot tie down, core bumps may protrude through the sheath, resulting in "core pops".

It is an object of this invention to provide a surgical cord possessing improved characteristics, e.g., reduced incidence of so called "core pops", a more uniform diameter, and at the same time providing good flexibility or so called "hand".

SUMMARY OF THE INVENTION

We have discovered a surgical cord comprising a sheath and an interlocked multifilament core.

DETAILED DESCRIPTION OF THIS INVENTION

The surgical cords of this invention provide surgical cords that simultaneously exhibit good flexibility ("good hand") and at least one improved property relative to a sutures of substantially equivalent size, the improved property being that of core pop free surgical cord or a more uniform diameter. This surgical cords can be used in a variety of surgical applications including but not limited to sutures, ligatures, artificial tendons and ligaments, tissue scaffolds, woven or knitted surgical meshes and reinforcing components in surgical composites.

Figure 3:
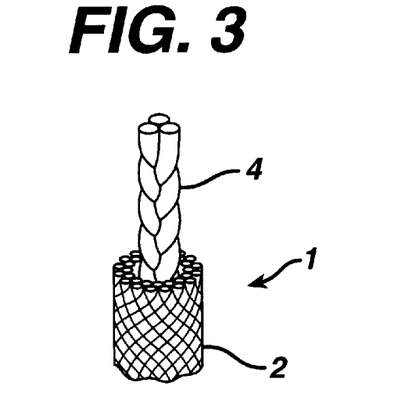
FIG. 3 is an enlarged perspective view of one embodiment of the present invention illustrating a surgical cord having a braided sheath and braided core.
Figure 3A:
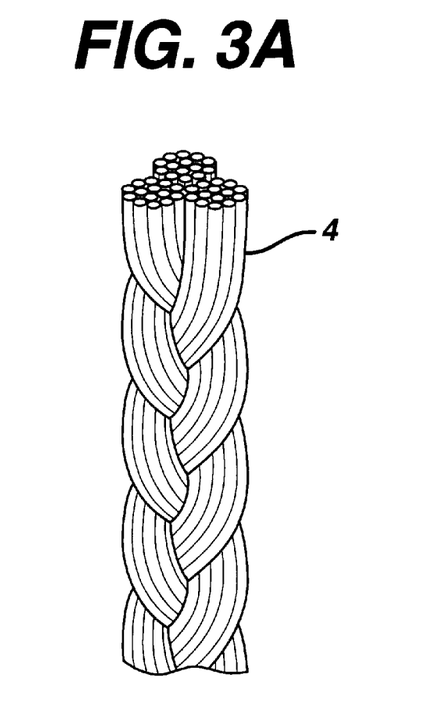
FIG. 3A is an enlarged view of the interlocking core of the surgical cord. The core of this surgical core is braided.

The term "surgical cord" is intended to include biocompatible surgical cords having a tubular sheath of interlocking yarns and a core of interlocking yarns. FIG. 3 illustrates a surgical cord 1 having a sheath 2 and a core 4. The term "interlocking yarns" refers to a textile structure in which the individual yarns have been locked into place by braiding or knitting as distinguished from twisted or plied cores that are commonly used in standard suture construction today. The sheath and core may be independently either braided or knitted. The sheath and core may be made of the same or different yarns; the yarns may be nonabsorbable or absorbable. Additionally, the yarns can be heterologous yarns as are described in U.S. Pat. No. 5,314,446 issued on May 24, 1994 hereby incorporated by reference herein.

The characteristics of the surgical cord of this invention, apart from the material of its construction, are (1) overall denier or the cord; (2) the sheath pick count (or number of crossovers of individual sheath yarns per linear inch of cord); (3) the core pick count (or number of crossovers of individual core yarns per linear inch of core yarn); (4) the number of yarns making up the sheath; (5) the number of yarns making up the core; and (6) the denier of the individual filaments comprising each yarn.

The overall denier of the surgical cord can vary but will generally be in the range of from about 50 to about 8,000 denier. For use as sutures the overall denier will generally range from about 200 denier to about 6,000 denier and more preferably will range from about 350 denier to about 4,000 denier.

Tubular Sheath

The tubular sheath can be braided or knitted. Methods for braiding yarns are well known in the art for example see U.S. Pat. Nos. 5,662,682; 5,456,697; 5,306,289; 5,261,886; 5,181,923; 5,133,738; and 5,019,093 (all hereby incorporated by reference herein). Suitable braiding equipment for manufacturing these surgical cords can be obtained from the following illustrative list of manufacturers New England Butt (USA), Ratera (Spain), Steeger (Germany), Hertzog (Germany), and Hacoba (formerly Krenzler of Germany). The braiding construction of the sheath may follow conventional braiding constructions for tubular braids. For example, for surgical cords that are braided the sheath pick count can vary from about 30 to about 100 crossovers/inch and preferably will range from about 40 to about 60 crossovers/inch and most preferably will range from about 45 to 55 crossovers/inch.

The selection of the number of sheath yarns to be used to make a surgical cord depends on a variety of factors such as: the desired diameter of the tubular sheath, the denier of the yarn that is being used for the sheath and the denier of the individual filaments of the yarn. The surgical cord can be constructed from as few as 3 sheath yarns and as many as 48 sheath yarns. Preferably the sheath yarns will range from about 3 to about 24 for most applications. Numerous braid patterns can be used to braid the sheath. For example, a braid pattern of "one yarn over one yarn under" or "two yarns over and two yarns under" could be used. Examples of suitable braided sheaths that could be used as sheaths are described in Table 1.

TABLE 1

| Suture size | Sheath Number of Yarns | Pick Count | Denier of Individual Filaments (DPF)[1] | Overall Suture Denier |
| --- | --- | --- | --- | --- |
| 5 | 12–48 | 30–80 | 1–10 | 4000–5000 |
| 3 | 12–36 | 30–80 | 1–10 | 3500–4000 |
| 2 | 12–36 | 30–80 | 1–10 | 2700–3500 |
| 1 | 12–36 | 30–80 | 1–10 | 2000–2700 |
| 0 | 12–36 | 30–80 | 1–10 | 1200–2000 |
| 2/0 | 8–32 | 30–100 | 1–10 | 800–1200 |
| 3/0 | 8–20 | 30–100 | 1–10 | 500–800 |
| 4/0 | 8–20 | 30–100 | 1–10 | 300–500 |
| 5/0 | 4–16 | 30–100 | 1–10 | 200–300 |
| 6/0 | 3–16 | 30–100 | 1–10 | 125–200 |

[1]DPF is the abbreviation for denier per filament.

The tubular sheath for surgical cords may also be knitted. A knitted tube can be made by a method of circular fabric construction by a series of interlocking loops of one or more yarns. The type of knitting for the tube will be weft knitting in which one continuous thread runs crosswise and the yarn makes all of the loops in one course. Although weft knitting is comprised of circular and flat knitting, the knitted tubes will be constructed from circular knitting machines. The fabric on a circular knitter is produced with the threads running continuously around the fabric. Methods for knitting yarns are well known. Suitable knitting equipment for manufacturing the sheaths of these surgical cords includes but is not limited to a Harry Lucas Knitting Machine or a Meyer Knitting Machine (manufactured by Karl Meyer Knitting Equipment of Germany). Using these machines, the knitting is performed vertically with the feeder spools on an overhead creel, which feeds the yarn into the knitting section. The interlocking core would also be feed from over head in this type of machine into the sheath as it was being formed. The surgical cord would then be gathered on a take up spool at the bottom of the machine. Examples of suitable knitted sheaths are described in Table 2 below.

TABLE 2

| Suture Size | Sheath Yarns | Sheath Wale & Course Count | Denier of Individual Filaments (DPF)[1] | Overall Suture Denier |
| --- | --- | --- | --- | --- |
| 5 | 12–24 | 10–30/8–15 | 1–10 | 4000–5000 |
| 3 | 12–24 | 10–30/8–15 | 1–10 | 3500–4000 |
| 2 | 12–16 | 10–30/8–15 | 1–10 | 2700–3500 |
| 1 | 12–16 | 10–30/8–15 | 1–10 | 2000–2700 |
| 0 | 12–16 | 10–30/8–15 | 1–10 | 1200–2000 |
| 2–0 | 8–16 | 10–30/8–15 | 1–10 | 800–1200 |
| 3–0 | 6–16 | 10–30/8–15 | 1–10 | 500–800 |
| 4–0 | 6–12 | 10–30/8–15 | 1–10 | 300–500 |
| 5–0 | 4–8 | 10–30/8–15 | 1–10 | 200–300 |

[1]DPF is the abbreviation for denier per filament.

Core

The core can be interlocked by braided or knitted. It is preferred that the core be interlocked by braiding. Suitable techniques for making a braided core are well known in the art and include conventional braid construction as well as spiral or solid braids described in U.S. Pat. Nos. 4,959,069 and 5,059,213 (both hereby incorporated by reference herein). The pick count (number of crossovers of individual core yarns per linear inch) of a surgical cord with a braided core will vary from about 5 to about 40 crossovers/inch with about 15 to about 30 crossovers being preferred.

The number of the core yarns depends on a variety of inter related factors the overall denier of the surgical cord, the sheath denier, core denier and the yarn used to make the core. Therefore, the braided cores within surgical cords can be constructed from as few as 3 core yarns and as many as about 24 core yarns. Numerous braid patterns can be used to braid the core. For example the braid pattern could be "one yarn over one yarn under" or "two yarns over and two yarns under". Table 3 presents some the currently preferred braiding constructions for braided cores.

TABLE 3

| Suture size | Core Number of Yarns | Pick Count | Denier of Individual Filaments (DPF) | Core Denier |
| --- | --- | --- | --- | --- |
| 5 | 4–24 | 5–40 | 1–10 | 2500–3000 |
| 3 | 4–24 | 5–40 | 1–10 | 2000–2500 |
| 2 | 4–24 | 5–40 | 1–10 | 1500–2000 |
| 1 | 3–16 | 5–40 | 1–10 | 1000–1500 |
| 0 | 3–16 | 5–40 | 1–10 | 500–1000 |
| 2/0 | 3–12 | 5–40 | 1–10 | 300–650 |
| 3/0 | 3–8 | 5–40 | 1–10 | 150–350 |
| 4/0 | 3–8 | 5–40 | 1–10 | 80–150 |
| 5/0 | 3–6 | 5–40 | 1–10 | 30–100 |
| 6/0 | 3–6 | 5–40 | 1–10 | 20–80 |

[1]DPF is the abbreviation for denier per filament.

The cores for surgical cords may also be knitted. A knitted core also can be made by a method of circular fabric construction by a series of interlocking loops of one or more yarns. The type of knitting for the core will be weft knitting in which one continuous thread runs crosswise and the yarn making all of the loops in one course. Suitable equipment for weft knitting has already been described. Table 4 presents some the currently preferred knitting constructions for knitted coresе.

TABLE 4

| Suture Size | Core Yarns | Core Wale & Course Count | Denier of Individual Filaments (DPF) | Core Denier |
|---|---|---|---|---|
| 5 | 3–8 | 5–20/2–12 | 1–10 | 2500–3000 |
| 3 | 3–8 | 5–15/2–10 | 1–10 | 2000–2500 |
| 2 | 3–8 | 5–15/2–10 | 1–10 | 1500–2000 |
| 1 | 3–6 | 5–15/2–10 | 1–10 | 1000–1500 |
| 0 | 3–6 | 5–15/2–8 | 1–10 | 500–1000 |
| 2–0 | 3–6 | 5–15/2–8 | 1–10 | 300–650 |
| 3–0 | 3–6 | 5–15/2–6 | 1–10 | 150–350 |
| 4–0 | 3–4 | 5–12/2–4 | 1–10 | 80–150 |
| 5–0 | 3–4 | 5–10/2–4 | 1–10 | 30–100 |

[1]DPF is the abbreviation for denier per filament.

The following tables present our currently preferred constructions for the inventive surgical cords.

Table 5 describes a surgical cord with multifilament interlocking braided sheath and interlocking core constructions.

TABLE 5

| Suture size | Sheath Number of Yarns | Sheath Pick Count | Core Number of Yarns | Core Pick Count | Denier of Individual Filaments (DFP) | Overall Suture Denier | Core Denier |
|---|---|---|---|---|---|---|---|
| 5 | 12–24 | 30-80 | 4–24 | 5-40 | 1-10 | 4000–5000 | 2500–3000 |
| 3 | 12–24 | 30-80 | 4–24 | 5-40 | 1-10 | 3500–4000 | 2000–2500 |
| 2 | 12–20 | 30-80 | 4–24 | 5-40 | 1-10 | 2700–3500 | 1500–2000 |
| 1 | 12–20 | 30-80 | 3–16 | 5-40 | 1-10 | 2000–2700 | 1000–1500 |
| 0 | 12–20 | 30-80 | 3–16 | 5-40 | 1-10 | 1200–2000 | 500–1000 |
| 2/0 | 8–16 | 30-100 | 3–12 | 5-40 | 1-10 | 800–1200 | 300–650 |
| 3/0 | 6–16 | 30-100 | 3–8 | 5-40 | 1-10 | 500–800 | 150–350 |
| 4/0 | 6–12 | 30-100 | 3–8 | 5-40 | 1-10 | 300–500 | 80-150 |
| 5/0 | 4–8 | 30-100 | 3–6 | 5-40 | 1-10 | 200–300 | 30–100 |
| 6/0 | 4–6 | 30-100 | 3–6 | 5-40 | 1-10 | 125–200 | 20–80 |

Table 6 describes a preferred surgical cord with a multifilament interlocking braided sheath and core constructions:

TABLE 6

| Suture size | Sheath Number of Yarns | Sheath Pick Count | Core Number of Yarns | Core Pick Count | Denier of Individual Filaments (DFP) | Overall Suture Denier | Core Denier |
|---|---|---|---|---|---|---|---|
| 5 | 12–20 | 40-60 | 8–20 | 5-30 | 1-3 | 4000–5000 | 2500–3000 |
| 3 | 12–20 | 40-60 | 8–20 | 5-30 | 1-3 | 3500–4000 | 2000–2500 |
| 2 | 12–20 | 40-60 | 8–16 | 5-30 | 1-3 | 2700–3500 | 1500–2000 |
| 1 | 12–20 | 40-60 | 3–16 | 5-30 | 1-3 | 2000–2700 | 1000–1500 |
| 0 | 12–20 | 40-60 | 3–12 | 5-30 | 1-3 | 2000–1200 | 500–1000 |
| 2/0 | 8–16 | 40-60 | 3–12 | 5-30 | 1-3 | 800–1200 | 300–650 |
| 3/0 | 6–16 | 40-60 | 3–8 | 5-30 | 1-3 | 500–800 | 150–350 |
| 4/0 | 6–12 | 50-80 | 3–8 | 5-30 | 1-3 | 300–500 | 80–150 |
| 5/0 | 4–8 | 50-80 | 3–6 | 5-30 | 1-3 | 200–300 | 30–100 |
| 6/0 | 4–6 | 50-80 | 3–6 | 5-30 | 1-3 | 125–200 | 20–80 |

Table 7 describes current preferred braided surgical cord constructions, possessing braided cores with the pick count of less than 30 ppi (preferred) for filaments made from about 5/95 glycolide/lactide copolymer:

TABLE 7

| Suture size | Sheath | | Core | | Denier of | | |
|---|---|---|---|---|---|---|---|
| | Number of Yarns ± 2 | Pick Count ± 5 | Number of Yarns ± 2 | Pick Count ± 5 | Individual Filaments (DP) ± 0.4 | Overall Suture Denier ± 15% | Core Denier ± 15% |
| 5 | 16 | 44-50 | 8 | 18-24 | 1.6 | 4700 | 1600 |
| 2 | 16 | 44-50 | 6 | 18-24 | 1.6 | 2800 | 800 |
| 1 | 16 | 44-50 | 6 | 18-24 | 1.6 | 2200 | 600 |
| 0 | 16 | 44-50 | 6 | 18-24 | 1.6 | 1700 | 400 |
| 2/0 | 12 | 44-50 | 4 | 18-24 | 1.6 | 1150 | 320 |
| 3/0 | 8 | 44-50 | 3 | 18-24 | 1.6 | 700 | 200 |
| 4/0 | 8 | 44-50 | 3 | 18-24 | 1.6 | 500 | 120 |
| 5/0 | 8 | 44-50 | 3 | 18-24 | 1.6 | 300 | 45 |

Numerous biocompatable absorbable and nonabsorbable materials can be used to make the yarns. Suitable nonabsorbable materials for use in sutures include, but are not limited to, cotton, linen, silk (although silk is referred to as a nonabsorbable material, it is broken down in the human body), polyamides (e.g. polyhexamethylene adipamide (nylon 66), polyhexamethylene sebacamide (nylon 610), polycapramide (nylon 6), polydodecanamide (nylon 12) and polyhexamethylene isophthalamide (nylon 6I), copolymers and blends thereof), polyesters (e.g. polyethylene terephthalate, polybutyl terphthalate (e.g. as described in EPA 287,899 and EPA 448,840), copolymers (e.g. as described in U.S. Pat. No. 4,314,561; Re 32,770; U.S. Pat. Nos. 4,224,946; 5,102,419 and 5,147,382) and blends thereof), fluoropolymers (e.g. polytetrafluoroethylene and polyvinylidene fluoride copolymers (e.g. as described in U.S. Pat. No. 4,564,013) and blends thereof) polyolefins (e.g. polypropylene including isotactic and syndiotactic polypropylene and blends thereof, as well as, blends composed predominately of isotactic or syndiotactic polypropylene blended with heterotactic polypropylene and polyethylene) and blends thereof. Suitable absorbable sutures include but are not limited aliphatic polyesters (e.g. absorbable polylactones, polyoxaesters, polyoxaamides polyoxaesters containing amido groups, polyalkylene oxalates, copolymers and blends thereof).

Although natural fibers such as cotton and linen may be used to make sutures, silk is one of the most preferred natural fiber for the manufacture of sutures. Raw silk consists of two filaments that are held together by seracin (silk glue). For surgical sutures the silk is degummed (the seracin is removed) and the resulting single filaments are used to manufacture the sutures. The denier per filament (dpf) of individual silk fibers will range from about 0.8 to about 2.0. For suture manufacture it is common to used silk with a dpf of from about 0.8 to about 1.6 and more preferably a dpf of from about 0.8 to about 1.4. The best grades of silk are easily obtainable from suppliers in China and Japan.

Polyesters are also well known commercially available synthetic polymers that may be used to make sutures. The most preferred polyester for making sutures is polyethylene terephthalate. Generally, polyethylene terephthalate polymers used to make sutures will have a weight average molecular weight of greater than 30,000 preferably greater than 40,000 and most preferably in the range of from about 42,000 to about 45,000. The filaments formed from these polymers should have a tenacity of greater than 5 grams/denier and preferably greater than 7 grams/denier. Polyethylene terephthalate yarns are commonly available from a variety of commercial fiber suppliers (such as E.I. DuPont and Hoechst Celanese). Preferred are commercially available filaments that may be purchased from Hoechst Celanese under the trademark Trevira® High Tenacity type 712 and 787 polyester yarns.

A variety of fluoropolymers may also be used to make sutures such as polytetrafluoroethylene and polyvinylidene fluoride (i.e. as in U.S. Pat. No. 4,052,550), copolymers and blends thereof. Currently the preferred are the fluoro polymers blends of polyvinylidene fluoride homopolymer and polyvinylidene fluoride and hexafluoropropylene copolymer which is described in U.S. Pat. No. 4,564,013 hereby incorporated by reference herein.

As previously stated the term polypropylene for the purposes of this application include isotactic and syndiotactic polypropylene (such as is described in U.S. Pat. No. 5,269,807 hereby incorporated by reference herein) and blends thereof, as well as, blends composed predominantly of isotactic or syndiotactic polypropylene blended with heterotactic polypropylene and polyethylene (such as is described in U.S. Pat. No. 4,557,264 issued Dec. 10, 1985 assigned to Ethicon, Inc. hereby incorporated by reference) and copolymers composed predominantly of propylene and other alpha-olefins such as ethylene (which is described in U.S. Pat. No. 4,520,822 issued Jun. 4, 1985 assigned to Ethicon, hereby incorporated by reference). The preferred polypropylene material for making sutures is isotactic polypropylene without any other polymers blended or monomers copolymerized therein. The preferred method for preparing the flexible polypropylene sutures of the present invention utilizes as the raw material pellets of isotactic polypropylene homopolymer having a weight average molecular weight of from about 260,00 to about 420,000. Polypropylene of the desired grade is commercially available in both powder and pellet form.

Particularly well suited absorbable polymers for the purpose of this invention are aliphatic polyesters which include but are not limited to homopolymers and copolymers of lactide (which includes D-, L-, lactic acid and D-, L- and meso lactide), glycolide (including glycolic acid), ε-caprolactone, p-dioxanone (1,4-dioxan-2-one which is described in U.S. Pat. No. 4,052,988), alkyl substituted derivatives of p-dioxanone (i.e. 6,6-dimethyl-1,4-dioxan-2-one which is described in U.S. Pat. No. 5,703,200 assigned to Ethicon and hereby incorporated by reference), trimethylene carbonate (1,3-dioxan-2-one), alkyl substituted derivatives of 1,3-dioxanone (which are described in U.S. Pat. No. 5,412,068 incorporated herein by reference), δ-valerolactone, β-butyrolactone, γ-butyrolactone, ε-decalactone, hydroxybutyrate, hydroxyvalerate, 1,4-dioxepan-2-one (described in U.S. Pat. No. 4,052,988 and its dimer 1,5,8,12-tetraoxacyclotetradecane-7,14-dione which is described in U.S. Pat. No. 5,442,032 assigned to Ethicon and hereby incorporated herein by reference), 1,5-dioxepan-2-one, and polymer blends thereof. Preferred suture materials include but are not limited to copolymers of trimethylene carbonate, ε-caprolactone and glycolide (such as are described in U.S. Pat. Nos. 5,431,679 and 5,854,383 hereby incorporated by reference) and copolymers of p-dioxanone, trimethylene carbonate and glycolide and copolymers of lactide and p-dioxanone. Preferred are suture compositions derived from lactide and glycolide sometimes referred to herein as simply homopolymers and copolymers of lactide and glycolide and copolymers of glycolide and ε-caprolactone i.e. as described in U.S. Pat. Nos. 5,133,739; 4,700,704 and 4,605,730), most preferred are 95/5 mole percent copolymers of poly(lactide-co-glycolide) and 10/90 mole percent copolymers of poly(lactide-co-glycolide).

Yarns can be made from the following conventional spinning processes such as melt spinning processes or solution spinning. After spinning the yarns may be quenched, treated with a spin finish, drawn and annealed as is known in the art.

The yarns should be made up of filaments having a denier in the range of from about 0.2 to about 10 and preferably a denier from about 0.8 to about 6 and more preferably a denier of from about 1 to about 3. The filaments are commonly extruded in bundles (yarns) having a denier in the range of from about 10 to about 500 denier and preferably 20 to 350 denier. The yarns may be twisted, entangled (such as rotoset or air jet entangled) or textured. The yarns may be twisted to have in the range of from about 2 to about 15 turns per inch (TPI).

After the surgical cord is fabricated, it may be scoured, annealed, coated with a lubricant, attached to a needle, sterilized and packaged. Additionally, different coating could be applied to the core and sheath to maximize the surgical cord's properties.

Currently it is preferred to coat the surgical cord with a lubricant and then heat set the surgical cord as is described in the U.S. Application entitled, BRAIDED SUTURE WITH IMPROVED KNOT STRENGTH AND PROCESS TO PRODUCE SAME, Ser. No. 09/159,025 which was filed on Sep. 23, 1998 and assigned to Ethicon Inc which is hereby incorporated by reference herein.

Alternatively, as previously mentioned the surgical cord could be further processed into other surgical devices such as knitted or woven surgical meshes and the like or used to form textile tissue scaffolds or composite materials. Sterilization can be performed by any conventional means, however, it is preferred to sterilize using ethylene oxide to avoid possible changes in properties that would occur if gamma sterilization was used.

Preliminary data also suggests that surgical cords made from absorbable polymers may unexpectedly have extended BSR (breaking strength retention) profiles as compared to conventional surgical sutures. It is theorized that the surgical cord structure may actually hydrolyze slower thereby retaining its strength longer than conventional sutures. In any event surgical cords made from lactone based polymers with a high lactide content (greater than 85 mole percent and more preferably greater than 90 mole percent) such as 95/5 poly(lactide-co-glycolide) copolymers may be used in a variety of surgical settings where a long term suture is desired. Surgical cords with high lactide content may also be useful in patients with compromised wound healing, because of the long term retention of strength allows the surgical cord to approximate the tissue long enough for the approximated tissue to heal.

The invention will be better understood by reference to the following non-limiting Examples:

EXAMPLES

Example 1

Conventional multifilament braided sutures have cores. The cores are generally twisted, plied, or flat yarn cores. Sutures with these constructions exhibit good "hand" but "core pop" readily.

A size 1 suture (95/5 Lactide/Glycolide) is used to illustrate unique construction differences in Table 8.

TABLE 8

| Suture Size | Sheath | | Core | | Denier of | | |
| | Denier, Number of Yarns | Pick Count | Denier, Number of Yarns | Pick Count | Individual Filaments (DPF)[1] | Overall Suture Denier | Core Denier |
| --- | --- | --- | --- | --- | --- | --- | --- |
| 1 | 100 × 1/16 | 48 | 100 × 3/2 | N/A[2] | 1.6 | 2200 | 600 |

[1]DPF means denier per filament.
[2]N/A means not appropriate because the core yarn is not interlocked.

The braided suture described above was produced using conventional braiding techniques. The core yarn was prepared by plying and twisting three 100 denier yarns together. A twist was applied to these yarns in the range of 3–6 tpi. The sheath yarn was also twisted in the range of 3–6 tpi. 16 braider bobbins were wound, each containing a 100 denier yarn of equal length. A 16 carrier New England Butt braider is set up with 16×100 denier sheath and two 100×3 core yarns, which are fed through the tubular sheath. The braider was set up to generate 48 picks or yarn crossovers per inch.

Example 2

This example describes a multifilament braided suture having a braided core. The braided core has a pick count of about 48. Sutures with braided cores having a pick count over about 40 exhibit reduced "core popping", but unfortunately give a poor "hand", because the sutures are relatively stiff.

TABLE 9

| Suture Size | Sheath Denier, Number of Yarns | Pick Count | Core Denier, Number of Yarns | PPI[1] | Denier of Individual Filaments (DPF)[2] | Overall Suture Denier | Core Denier |
|---|---|---|---|---|---|---|---|
| 1 | 100 × 1/16 | 48 | 100 × 1/6 | 48 | 1.6 | 2200 | 600 |

[1]PPI is picks per inch.
[2]DPF is denier per filament.

The braided sutures described in this table were produced using conventional braiding equipment. The sheath and core yarns were prepared by twisting 100 denier yarn. The twist was applied to the yarn in the range of from 3–6 tpi. Twenty-two braider bobbins are wound, each containing a 100 denier yarn of equal length. A 12 carrier New England Butt braider was set up to produce a core, with 6×100 denier bobbins, skipping each other carrier. Only ½ of the carriers were utilized for making the core. The braider was set up to generate 48 picks or yarn crossovers per inch. A New England Butt braider with 16 carriers was set up with 16×100 denier sheath and 100×6 braided core, which was fed through the tubular sheath. The braider was set up to generate 48 picks or yarn crossovers per inch.

Example 3

This example describes a multifilament braided sugical cord having a braided core with a pick counts between 5 and 40. Surgical cords with these constructions advantageously exhibit reduced "core popping" and good "hand".

TABLE 10

| Suture Size | Sheath Denier, Number of Yarns | Pick Count | Core Denier, Number of Yarns | PPI[1] | Denier of Individual Filaments (DPF)[2] | Overall Suture Denier | Core Denier |
|---|---|---|---|---|---|---|---|
| 1 | 100 × 1/16 | 48 | 100 × 1/6 | 48 | 1.6 | 2200 | 600 |

[1]PPI is picks per inch.
[2]DPF is denier per inch.

The surgical cord described in Table 10 was produce using conventional braiding equipment. The sheath and core yarns were prepared by twisting 100 denier yarn. The twist applied to the yarn was in range of 3–6 tpi. 22 braider bobbins were wound, each containing a 100 denier yarn of equal length. A New England Butt braider with 12 carrier was set up to produce a core, with 6×100 denier bobbins, skipping each other carrier. Only ½ of or carriers were utilized for making the core. The braider was set up to generate 18 picks or yarn crossovers per inch. A New England Butt braider with 16 carrier was set up with 16×100 denier sheath and 100×6 braided core, which was fed through the tubular sheath. The braider was set up to generate 48 picks or yarn crossovers per inch.

Example 4

A comparison of suture properties, such as visual for "core popping", and bending stiffness are presented in a Table 11 below:

TABLE 11

| | Example 1 Conventional Braid | Example 2 Suture with a Braided Core, PPI is >40 | Example 3 Surgical Cord with a Braided Core, PPI is <40 |
|---|---|---|---|
| Core Popping | 4/5 | 0 | 0 |
| Bending Stiffness (grams) | 14.85 | 10.86 | 9.76 |

1. Core Popping Test

Figure 4:
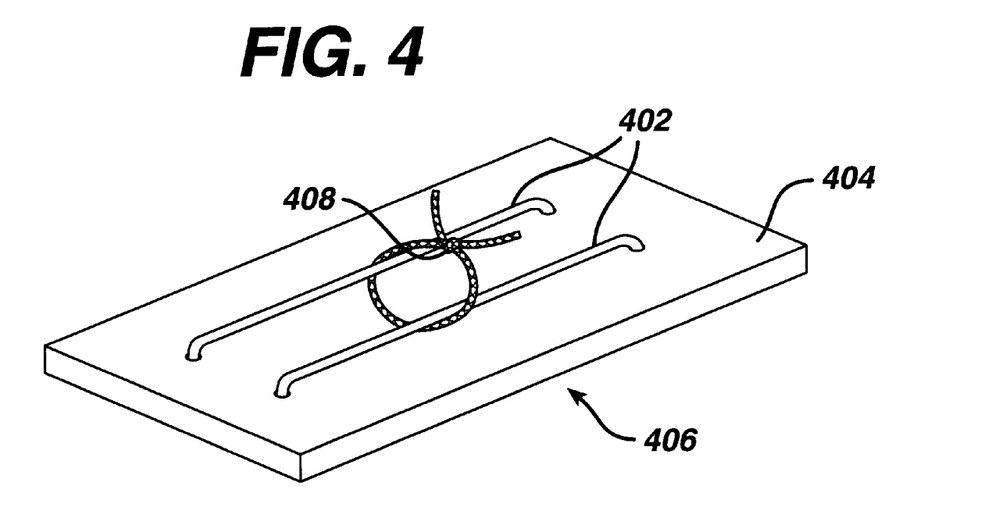
FIG. 4 is a perspective view of a device for tying knots.

Five 27 inch suture strands from each lot were visually examined for core pops before and after a subjective tie down test. A square knot was used in this test to tie 4 throws, using a tie board. The tie board 406 is illustrated in FIG. 4. The tie board consists of two rubber bands 402 of about ¼ inch diameter, which are stretched substantially parallel to each other and anchored to the board 404. The distance between the two rubber bands is about ½ inch. When the knot 408 is tied, the two rubber bands are forced to come in close contact with each other. At the same time, due to the elastic properties of the rubber bands, a counter-force is generated that pulls the knot apart.

2. Bending Stiffness Test

Five suture strands 1.5 inch in length were prepared from each lot for testing. A special fixture (described below) was used with the Instron Tensile Tester (Model 4201) to measure the resistance of the force required to pull the suture through the opening in the fixture. A load cell of 500 g was used for this test. The crosshead speed was one inch per minute. The information from the test was gathered electronically.

Figure 5:
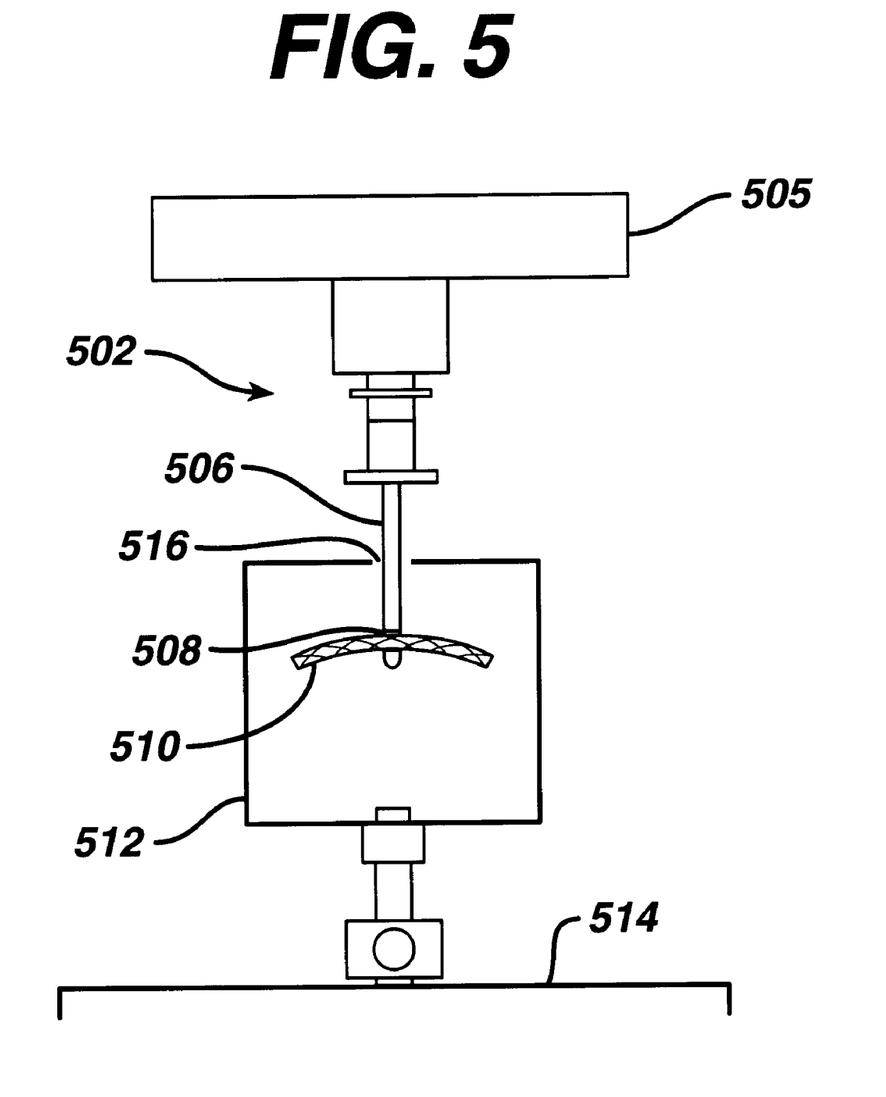
FIG. 5 is a schematic view of a device for testing the bending stiffness.

The upper portion of this fixture was illustrated in FIG. 5. The fixture 502 consists of the metal rod 506 with a passage 508 at the end of the rod for threading the suture 510 through. The upper end of the rod was connected to load cell 505. The lower portion of the fixture consists of a bracket 512 attached to the machine base 514. That bracket has an opening 516 is 10 mm, which was slightly larger than the diameter of rod 506. The center of this opening 516 was lined up with the center of the metal rod.

Five samples of 1.5 inch each of the suture was prepared. Each sample was inserted through passage 8 in the metal rod until length of suture on each side of opening was about the same. Then, the crosshead was getting started and the suture was pulled through opening in the bracket. When the suture sample was pulled through the opening in the bracket, the resistance in grams is being recorded. Five samples were measured and the results were averaged to provide the reported values.

We claim:

1. A surgical cord comprising biocompatible surgical cord having an interlocking sheath and an interlocked multifilament core selected from the group consisting of braided cores having a pick count of from about 5 to about 40 crossovers/inch and knitted cores.

2. The surgical cord of claim 1 wherein the interlocking sheath is selected from the group consisting of braided sheaths and knitted sheaths.

3. The surgical cord of claim 1 wherein the interlocking sheath is bioabsorbable.

4. The surgical cord of claim 3 wherein the interlocking core is nonabsorbable.

5. The surgical cord of claim 1 wherein the interlocking sheath is nonabsorbable.

6. The surgical cord of claim 5 wherein the interlocking core is absorbable.

7. The surgical cord of claim 1 wherein the interlocking sheath and interlocking core are nonabsorbable.

8. The surgical cord of claim 1 wherein the interlocking sheath and interlocking core are absorbable.

9. The surgical cord of claim 1 wherein the interlocking sheath is braided.

10. The surgical cord of claim 9 wherein the interlocking core is braided.

11. The surgical cord of claim 1 wherein the interlocking sheath is braided as described below:

| Suture size | Sheath Number of Yarns | Pick Count | Denier of Individual Filaments (DPF) | Overall Suture Denier |
|---|---|---|---|---|
| 5 | 12–48 | 30–80 | 1–10 | 4000–5000 |
| 3 | 12–36 | 30–80 | 1–10 | 3500–4000 |
| 2 | 12–36 | 30–80 | 1–10 | 2700–3500 |
| 1 | 12–36 | 30–80 | 1–10 | 2000–2700 |
| 0 | 12–36 | 30–80 | 1–10 | 1200–2000 |
| 2/0 | 8–32 | 30–100 | 1–10 | 800–1200 |
| 3/0 | 8–20 | 30–100 | 1–10 | 500–800 |
| 4/0 | 8–20 | 30–100 | 1–10 | 300–500 |
| 5/0 | 4–16 | 30–100 | 1–10 | 200–300 |
| 6/0 | 3–16 | 30–100 | 1–10 | 125–200. |

12. The surgical cord of claim 1 wherein the interlocking sheath is knitted as described below:

| Suture Size | Sheath Yarns | Sheath Wale & Course Count | Denier of Individual Filaments (DPF) | Overall Suture Denier |
|---|---|---|---|---|
| 5 | 12–24 | 10–30/8–15 | 1–10 | 4000–5000 |
| 3 | 12–24 | 10–30/8–15 | 1–10 | 3500–4000 |
| 2 | 12–16 | 10–30/8–15 | 1–10 | 2700–3500 |
| 1 | 12–16 | 10–30/8–15 | 1–10 | 2000–2700 |
| 0 | 12–16 | 10–30/8–15 | 1–10 | 1200–2000 |
| 2–0 | 8–16 | 10–30/8–15 | 1–10 | 800–1200 |
| 3–0 | 6–16 | 10–30/8–15 | 1–10 | 500–800 |
| 4–0 | 6–12 | 10–30/8–15 | 1–10 | 300–500 |
| 5–0 | 4–8 | 10–30/8–15 | 1–10 | 200–300. |

13. The surgical cord of claim 1 wherein the interlocking core is braided as described below:

| Suture size | Core Number of Yarns | Pick Count | Denier of Individual Filaments (DPF) | Core Denier |
|---|---|---|---|---|
| 5 | 4–24 | 5–40 | 1–10 | 2500–3000 |
| 3 | 4–24 | 5–40 | 1–10 | 2000–2500 |
| 2 | 4–24 | 5–40 | 1–10 | 1500–2000 |
| 1 | 3–16 | 5–40 | 1–10 | 1000–1500 |
| 0 | 3–16 | 5–40 | 1–10 | 500–1000 |
| 2/0 | 3–12 | 5–40 | 1–10 | 300–650 |
| 3/0 | 3–8 | 5–40 | 1–10 | 150–350 |
| 4/0 | 3–8 | 5–40 | 1–10 | 80–150 |
| 5/0 | 3–6 | 5–40 | 1–10 | 30–100 |
| 6/0 | 3–6 | 5–40 | 1–10 | 20–80. |

14. The surgical cord of claim 1 wherein the interlocking core is knitted as described below:

| Suture Size | Core Yarns | Core Wale & Course Count | Denier of Individual Filaments (DPF) | Core Denier |
|---|---|---|---|---|
| 5 | 3–8 | 5–20/2–12 | 1–10 | 2500–3000 |
| 3 | 3–8 | 5–15/2–10 | 1–10 | 2000–2500 |
| 2 | 3–8 | 5–15/2–10 | 1–10 | 1500–2000 |
| 1 | 3–6 | 5–15/2–10 | 1–10 | 1000–1500 |
| 0 | 3–6 | 5–15/2–8 | 1–10 | 500–1000 |
| 2–0 | 3–6 | 5–15/2–8 | 1–10 | 300–650 |
| 3–0 | 3–6 | 5–15/2–6 | 1–10 | 150–350 |
| 4–0 | 3–4 | 5–12/2–4 | 1–10 | 80–150 |
| 5–0 | 3–4 | 5–10/2–4 | 1–10 | 30–100. |

15. The surgical cord of claim 1 wherein the cord is made up of yarns that contain filaments formed from aliphatic polyesters selected from the group consisting of homopolymers and copolymers of lactide, glycolide, ε-caprolactone, p-dioxanone, alkyl substituted derivatives of p-dioxanone, trimethylene carbonate, alkyl substituted derivatives of 1,3-dioxanone, δ-valerolactone, β-lactone, γ-butyrolactone, ε-decalactone, hydroxybutyrate, hydroxyvalerate, 1,4-dioxepan-2-one, 1,5-dioxepan-2-one, and polymer blends thereof.

16. The surgical cord of claim 13 wherein the surgical cord is made from yarns formed from biocompatible filaments of a glycolide-co-lactide copolymer.

17. The surgical cord of claim 1 wherein the cord is made up of yarns that contain filaments formed from biocompatible nonabsorbable materials selected from the group consisting of cotton, linen, silk, polyamides, polyesters, fluoropolymers and polyolefins and blends thereof.

18. The surgical cord of claim 17 wherein the surgical cord is made from yarns formed from a bicompatible filaments of polyethylene terephthalate.

19. The surgical cord of claim 17 wherein the surgical cord is made from yarns formed from a bicompatible filaments of polybutylene terephthalate.

20. The surgical cord of claim 17 wherein the surgical cord is made from yarns formed from a bicompatible filaments of polyethylene.

21. The surgical cord of claim 17 wherein the surgical cord is made from yarns formed from a bicompatible filaments of polyvinylidene fluoride copolymers.

22. The surgical cord of claim 1 wherein the surgical cord is attached to a needle.

23. The surgical cord of claim 1 wherein the surgical cord is coated with a biocompatible lubricant.

24. The surgical cord of claim 1 wherein the surgical cord is formed into a tissue scaffold.

25. The surgical cord of claim 1 wherein the surgical cord is used to form a medical composite.

26. The surgical cord of claim 1 wherein the surgical cord is knitted into a mesh.

27. The surgical cord of claim 1 wherein the surgical cord is woven into a textile.

28. The surgical cord of claim 10 wherein the surgical cord is constructed as described below:

| Suture size | Sheath | | Core | | Denier of | | |
| | Number of Yarns | Pick Count | Number of Yarns | Pick Count | Individual Filaments (DFP) | Overall Suture Denier | Core Denier |
|---|---|---|---|---|---|---|---|
| 5 | 12–24 | 30-80 | 4–24 | 5-40 | 1-10 | 4000–5000 | 2500–3000 |
| 3 | 12–24 | 30-80 | 4–24 | 5-40 | 1-10 | 3500–4000 | 2000–2500 |
| 2 | 12–20 | 30-80 | 4–24 | 5-40 | 1-10 | 2700–3500 | 1500–2000 |
| 1 | 12–20 | 30-80 | 3–16 | 5-40 | 1-10 | 2000–2700 | 1000–1500 |
| 0 | 12–20 | 30-80 | 3–16 | 5-40 | 1-10 | 1200–2000 | 500–1000 |
| 2/0 | 8–16 | 30-100 | 3–12 | 5-40 | 1-10 | 800–1200 | 300–650 |
| 3/0 | 6–16 | 30-100 | 3–8 | 5-40 | 1-10 | 500–800 | 150–350 |
| 4/0 | 6–12 | 30-100 | 3–8 | 5-40 | 1-10 | 300–500 | 80–150 |
| 5/0 | 4–8 | 30-100 | 3–6 | 5-40 | 1-10 | 200–300 | 30–100 |
| 6/0 | 4–6 | 30-100 | 3–6 | 5-40 | 1-10 | 125–200 | 20–80. |

29. The surgical cord of claim 10 wherein the surgical cord is constructed as described below:

| Suture size | Sheath | | Core | | Denier of | | |
| | Number of Yarns | Pick Count | Number of Yarns | Pick Count | Individual Filaments (DFP) | Overall Suture Denier | Core Denier |
|---|---|---|---|---|---|---|---|
| 5 | 12–20 | 40-60 | 8–20 | 5-30 | 1-3 | 4000–5000 | 2500–3000 |
| 3 | 12–20 | 40-60 | 8–20 | 5-30 | 1-3 | 3500–4000 | 2000–2500 |
| 2 | 12–20 | 40-60 | 8–16 | 5-30 | 1-3 | 2700–3500 | 1500–2000 |
| 1 | 12–20 | 40-60 | 3–16 | 5-30 | 1-3 | 2000–2700 | 1000–1500 |
| 0 | 12–20 | 40-60 | 3–12 | 5-30 | 1-3 | 2000–1200 | 500–1000 |
| 2/0 | 8–16 | 40-60 | 3–12 | 5-30 | 1-3 | 800–1200 | 300–650 |
| 3/0 | 6–16 | 40-60 | 3–8 | 5-30 | 1-3 | 500–800 | 150–350 |
| 4/0 | 6–12 | 50-80 | 3–8 | 5-30 | 1-3 | 300–500 | 80–150 |
| 5/0 | 4–8 | 50-80 | 3–6 | 5-30 | 1-3 | 200–300 | 30–100 |
| 6/0 | 4–6 | 50-80 | 3–6 | 5-30 | 1-3 | 125–200 | 20–80. |

30. The surgical cord of claim 10 wherein the surgical cord is constructed as described below:

| Suture size | Sheath | | Core | | Denier of | | |
| | Number of Yarns ± 2 | Pick Count ± 5 | Number of Yarns ± 2 | Pick Count ± 5 | Individual Filaments (DP) ± 0.4 | Overall Suture Denier ± 15% | Core Denier ± 15% |
|---|---|---|---|---|---|---|---|
| 5 | 16 | 44-50 | 8 | 18-24 | 1.6 | 4700 | 1600 |
| 2 | 16 | 44-50 | 6 | 18-24 | 1.6 | 2800 | 800 |
| 1 | 16 | 44-50 | 6 | 18-24 | 1.6 | 2200 | 600 |
| 0 | 16 | 44-50 | 6 | 18-24 | 1.6 | 1700 | 400 |
| 2/0 | 12 | 44-50 | 4 | 18-24 | 1.6 | 1150 | 320 |
| 3/0 | >8 | 44-50 | 3 | 18-24 | 1.6 | 700 | 200 |
| 4/0 | 8 | 44-50 | 3 | 18-24 | 1.6 | 500 | 120 |
| 5/0 | 8 | 44-50 | 3 | 18-24 | 1.6 | 300 | 45. |

* * * * *

UNITED STATES PATENT AND TRADEMARK OFFICE
CERTIFICATE OF CORRECTION

PATENT NO. : 6,045,571
DATED : April 4, 2000
INVENTOR(S) : Donald G. Hill et al.

It is certified that error appears in the above-identified patent and that said Letters Patent is hereby corrected as shown below:

Column 16,
Table 3, third line from bottom, please delete ">" before the number "8"

Signed and Sealed this

Twenty-seventh Day of April, 2004

JON W. DUDAS
*Acting Director of the United States Patent and Trademark Office*